United States Patent [19]

Thieme et al.

[11] 4,353,904

[45] Oct. 12, 1982

[54] PHENYLPIPERAZINE DERIVATIVES OF 1,3,4-OXADIAZOLYLPHENOLS, AND THERAPEUTIC AGENTS CONTAINING THESE COMPOUNDS

[75] Inventors: Peter C. Thieme; Albrecht Franke, both of Wachenheim; Dieter Lenke, Ludwigshafen; Hans D. Lehmann, Hirschberg-Leutershausen; Josef Gries, Wachenheim, all of Fed. Rep. of Germany

[73] Assignee: BASF Aktiengesellschaft, Fed. Rep. of Germany

[21] Appl. No.: 228,370

[22] Filed: Jan. 26, 1981

[30] Foreign Application Priority Data

Feb. 13, 1980 [DE] Fed. Rep. of Germany ....... 3005287

[51] Int. Cl.³ .................. C07D 413/12; A61K 31/495
[52] U.S. Cl. ...................................... 424/250; 544/367
[58] Field of Search ......................... 544/367; 424/250

[56] References Cited

U.S. PATENT DOCUMENTS

| | | | |
|---|---|---|---|
| 3,502,668 | 3/1970 | Palazzo et al. | 544/367 |
| 3,787,411 | 1/1974 | Ruschig et al. | 544/367 |
| 3,856,794 | 12/1975 | Danilewicz et al. | 424/250 |
| 3,941,789 | 3/1976 | Renth et al. | 424/250 |

FOREIGN PATENT DOCUMENTS

1110360 4/1968 United Kingdom ................ 544/367

OTHER PUBLICATIONS

Maillard et al., Bull. Soc. Chim., France, (1966), pp. 376-381.

*Primary Examiner*—Anton H. Sutto
*Assistant Examiner*—Sharon A. Gibson
*Attorney, Agent, or Firm*—Keil & Witherspoon

[57] ABSTRACT

Novel phenylpiperazinylpropanols of 1,3,4-oxadiazolylphenols and their physiologically tolerated addition salts with acids, processes for their preparation, and pharmaceutical formulations which contain these compounds and are useful in the treatment of hypertonia.

6 Claims, No Drawings

PHENYLPIPERAZINE DERIVATIVES OF 1,3,4-OXADIAZOLYLPHENOLS, AND THERAPEUTIC AGENTS CONTAINING THESE COMPOUNDS

The present invention relates to novel phenylpiperazinylpropanols of 1,3,4-oxadiazolylphenols and their physiologically tolerated addition salts with acids, processes for their preparation, and pharmaceutical formulations which contain these compounds and are useful in the treatment of hypertonia.

German Laid-Open Application DOS No. 2,811,638 discloses aminopropanol derivatives of 1,3,4-oxadiazolylphenols, and describes their $\beta$-adrenolytic and hypotensive action. Furthermore, for example, the drug Urapidil, a uracil derivative containing an o-methoxyphenylpiperazinyl radical, is a known antihypertonic agent.

We have found that compounds of the general formula I

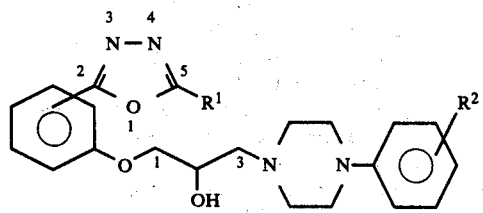

where $R^1$ is hydrogen or lower alkyl of 1 to 4 carbon atoms and $R^2$ is hydrogen, halogen, lower alkyl of 1 to 4 carbon atoms or lower alkoxy of 1 to 3 carbon atoms, and where the phenyl ring may contain one or two substituents $R^2$, and their addition salts with acids possess valuable pharmacological properties.

The 1,3,4-oxadiazol-2-yl radical may be in the o-, m- or p-position to the ether group, though the m-position is preferred.

Examples of straight-chain or branched alkyl $R^1$ of 1 to 4 carbon atoms are methyl, ethyl, n-propyl, isopropyl, n-butyl and tert.-butyl. Preferably, $R^1$ is hydrogen or methyl.

$R^2$ may be in the o-, m- or p-position to the piperazine substituent in the phenyl ring of the phenylpiperazine, and may, for example, be, as halogen, fluorine, chlorine, bromine or iodine, amongst which fluorine and chlorine in the p- or m-position are preferred, and, as lower alkoxy, methoxy, ethoxy, propoxy or isopropoxy, of which methoxy and ethoxy in the o-position are preferred.

Examples of phenyl radicals with two substituents $R^2$ are o,o'-dimethylphenyl and o,p-dimethoxyphenyl.

Accordingly, examples of compounds according to the invention, of the formula I, are: 1-[2-(1,3,4-oxadiazol-2-yl)-phenoxy]-3-[4-(2-methoxyphenyl)-piperazin-1-yl]-propan-2-ol, 1-[2-(5-methyl-1,3,4-oxadiazol-2-yl)-phenoxy]-3-[4-(2-methoxyphenyl)-piperazin-1-yl]-propan-2-ol, 1-[3-(1,3,4-oxadiazol-2-yl)-phenoxy]-3-[4-(2-methoxyphenyl)-piperazin-1-yl]-propan-2-ol, 1-[3-(1,3,4-oxadiazol-2-yl)-phenoxy]-3-[4-(2-ethoxyphenyl)-piperazin-1-yl]-propan-2-ol, 1-[3-(1,3,4-oxadiazol-2-yl)-phenoxy]-3-[4-(2-propoxyphenyl)-piperazin-1-yl]-propane-2-ol, 1-[3-(1,3,4-oxadiazol-2-yl)-phenoxy]-3-[4-(2-isopropoxyphenyl)-piperazin-1-yl]-propan-2-ol, 1-[3-(5-methyl-1,3,4-oxadiazol-2-yl)-phenoxy]-3-(4-phenyl-piperazin-1-yl)-propan-2-ol, 1-[3-(5-methyl-1,3,4-oxadiazol-2-yl)-phenoxy]-3-[4-(2-methoxyphenyl)-piperazin-1-yl]-propan-2-ol, 1-[3-(5-methyl-1,3,4-oxadiazol-2-yl)-phenoxy]-3-[4-(2-ethoxyphenyl)-piperazin-1-yl]-propan-2-ol, 1-[3-(5-methyl-1,3,4-oxadiazol-2-yl)-phenoxy]-3-[4-(4-fluorophenyl)-piperazin-1-yl]-propan-2-ol, 1-[3-(5-ethyl-1,3,4-oxadiazol-2-yl)-phenoxy]-3-[4-(2-methoxyphenyl)-piperazin-1-yl]-propan-2-ol, 1-[3-(5-ethyl-1,3,4-oxadiazol-2-yl)-phenoxy]-3-[4-(2-ethoxyphenyl)-piperazin-1-yl]-propan-2-ol, 1-[3-(5-ethyl-1,3,4-oxadiazol-2-yl)-phenoxy]-3-[4-(2-chlorophenyl)-piperazin-1-yl]-propan-2-ol, 1-[3-(5-propyl-1,3,4-oxadiazol-2-yl)-phenoxy]-3-[4-(2-methoxyphenyl)-piperazin-1-yl]-propan-2-ol, 1-[3-(5-tert.-butyl-1,3,4-oxadiazol-2-yl)-phenoxy]-3-[4-(2-methoxyphenyl)-piperazin-1-yl]-propan-2-ol, 1-[4-(1,3,4-oxadiazol-2-yl)-phenoxy]-3-[4-(4-fluorophenyl)-piperazin-1-yl]-propan-2-ol and 1-[4-(5-methyl-1,3,4-oxadiazol-2-yl)-phenoxy]-3-[4-(3-methoxyphenyl)-piperazin-1-yl]-propan-2-ol.

The novel compounds are prepared by a method wherein a 1,3,4-oxadiazol-2-yl-phenyl derivative of the general formula II

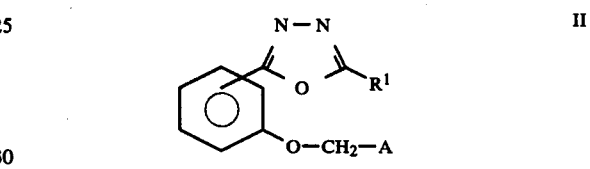

where $R^1$ has the meanings given for formula I and A is

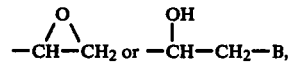

B being a nucleofugic leaving group, is reacted, in a conventional manner, with a phenylpiperazine of the general formula III

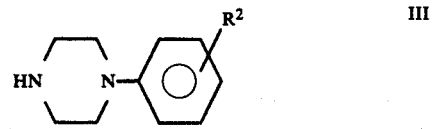

where $R^2$ has the meanings given for formula I, advantageously in a solvent and in the presence or absence of an acid acceptor, after which, if desired, the compound obtained is converted to the addition salt with a physiologically tolerated acid.

The leaving group B is preferably halogen, especially chlorine, bromine or iodine. Other examples of suitable nucleofugic leaving groups are aromatic and aliphatic sulfonic acid radicals, eg. the p-toluenesulfonic acid, p-bromobenzenesulfonic acid and methanesulfonic acid radical.

The reactions are carried out at from 10° to 120° C., ie. at room temperature or above, advantageously at from 50° to 120° C. The reactions may be carried out under atmospheric pressure or in a closed vessel under superatmospheric pressure, if necessary with heating to the stated temperature range.

The starting compounds may be reacted in the absence of a diluent or solvent. Advantageously, however, they are carried out in the presence of an inert diluent or solvent, for example a lower alcohol of 1 to 4 carbon atoms, eg. methanol, ethanol or a propanol, preferably isopropanol or ethanol, a lower saturated dialkyl ether, dialkyl glycol ether or cyclic ether, eg. diethyl ether, 1,2-dimethoxyethane, tetrahydrofuran or dioxane, an aromatic hydrocarbon, such as benzene or an alkylbenzene, eg. toluene or xylene, a saturated aliphatic hydrocarbon, eg. hexane, heptane or octane, a lower aliphatic ketone, eg. acetone, methyl ethyl ketone or methyl isobutyl ketone, a dialkylformamide, eg. dimethylformamide or diethylformamide, dimethylsulfoxide or water, or a mixture of the stated solvents.

Preferred solvents for the reaction of an epoxide of the formula II, for example of a 2,3-epoxypropoxyphenyl-1,3,4-oxadiazole, with a phenylpiperazine of the formula III are lower alcohols, especially ethanol and isopropanol, the reaction preferably being carried out at 50° C.–120° C. under atmospheric pressure. For the nucleophilic replacement of a radical B, preferred solvents are lower aliphatic ketones, eg. acetone, diethyl ketone, methyl isopropyl ketone and methyl isobutyl ketone, cyclic saturated ethers, especially tetrahydrofuran and dioxane, and dialkylformamides, eg. dimethylformamide, the reaction preferably being carried out at 90°–120° C. If desired, the reaction is carried out in the presence of a catalytic amount of sodium iodide or potassium iodide.

A mixture of the epoxide with a halohydrin may also be used as the starting compound of the formula II; such mixtures are, under certain conditions, formed in the industrial manufacture of the starting compounds of the formula II.

In an advantageous embodiment of the nucleophilic replacement of the radical B by the phenylpiperazine derivative used, the reaction is carried out in the presence of a base as an acid acceptor. Preferred bases are alkali metal hydroxides, carbonates, bicarbonates and alcoholates, and tertiary organic amines, eg. pyridine or trialkylamines, such as trimethylamine or triethylamine. Amongst the alkali metal compounds, those of sodium and potassium are preferred. The base is used in the stoichiometric amount or in slight excess. It can also be advantageous to use an excess of the phenylpiperazine derivative employed for the reaction, so that it serves, at the same time, as the acid acceptor.

The time required for completion of the reaction depends on the reaction temperature and is in general from 2 to 15 hours. The reaction product can be isolated in a conventional manner, for example by filtration, or by distilling the diluent or solvent from the reaction mixture. The compound obtained is purified in a conventional manner, for example by recrystallization from a solvent, by conversion to an addition compound with an acid, or by column chromatography.

The starting compounds of the formula (II) may be prepared by alkylating the 1,3,4-oxadiazolylphenols, which can be prepared as described in the literature (J. Maillard, M. Vincent and V. Van-Tri, Bull. Soc. Chim. France (1966), page 376 et seq) with an epihalohydrin or an α,ω-dihalo-propan-2-ol.

Suitable epihalohydrins are epichlorohydrin, epibromohydrin and epiiodohydrin, and suitable α,ω-dihalo-propan-2-ols are, in particular, 1,3-dichloropropan-2-ol and 1,3-dibromo-propan-2-ol.

The conversion of a 1,3,4-oxadiazolylphenol to a starting compound of the formula II is advantageously carried out at from 0° to 120° C. under atmospheric pressure, or in a closed vessel under superatmospheric pressure. Advantageously, the reaction is carried out in an inert diluent or solvent, for example a lower aliphatic ketone, eg. acetone, methyl ethyl ketone and methyl isobutyl ketone, a lower alcohol of 1 to 4 carbon atoms, such as methanol, ethanol, propanol or butanol, a saturated aliphatic or cyclic ether, eg. dialkyl ether, tetrahydrofuran or dioxane, a dialkylformamide, eg. dimethylformamide or diethylformamide, or hexamethylphosphorotriamide, or in an excess of the alkylating agent as the diluent or solvent.

Preferably, the reaction is carried out in the presence of a base as an acid acceptor. Suitable bases are alkali metal carbonates, bicarbonates, hydroxides, hydrides and alcoholates, especially those of sodium and potassium, basic oxides, eg. aluminum oxide and calcium oxide, and organic tertiary bases, eg. pyridine or lower trialkylamines, such as trimethylamine and triethylamine. The base may be used in a catalytic amount, or in the stoichiometric amount or slight excess relative to the alkylating agent employed.

Preferably, the 1,3,4-oxadiazolylphenols are reacted with epibromohydrin or 1,2-dibromopropan-2-ol in a solvent mixture comprising an ether and a polar aprotic solvent, especially tetrahydrofuran or hexamethylphosphorotriamide, at from 0° to 50° C.

The starting compounds of the formula II may be interconverted by a simple acid-base reaction. For example, a 2,3-epoxypropoxyphenyl-1,3,4-oxadiazole can be converted, by means of the corresponding halohydric acid, to a 2-hydroxy-3-halopropoxyphenyl-1,3,4-oxadiazole, the solvent or diluent used being a conventional solvent, but preferably an aliphatic or cyclic ether, eg. diethyl ether, tetrahydrofuran or dioxane, or a lower alcohol, eg. methanol, ethanol and propanol. On the other hand, a 2-hydroxy-3-halopropoxyphenyl-1,3,4-oxadiazole can be converted to the 2,3-epoxypropoxyphenyl-1,3,4-oxadiazole by means of a base, eg. an alkali metal hydroxide, carbonate, bicarbonate, alcoholate or hydride, a tertiary organic amine, eg. pyridine, or a tertiary aliphatic amine, especially trimethylamine or triethylamine, or piperidine. These reactions may be carried out at room temperature, but can be accelerated, or completed, by heating, for example to 60°–120° C. The reaction may be carried out under atmospheric pressure or in a closed vessel under superatmospheric pressure, with or without heating. The starting materials for these conversions may be isolated beforehand or be produced in situ and be further converted direct, without isolation and purification.

The novel compounds of the formula (I) have a chirality center on carbon atom 2 of the aliphatic side chain and are obtained as racemates, which can be separated into the optically active antipodes by conventional methods, for example by forming diastereomeric salts with optically active auxiliary acids, such as dibenzoyltartaric acid, camphor-10-sulfonic acid, ditoluyltartaric acid or 3-bromo-camphor-8-sulfonic acid.

If desired, a novel compound obtained may be converted to an addition salt with a physiologically tolerated acid. Examples of conventional physiologically tolerated organic and inorganic acids are, amongst inorganic acids, hydrochloric acid, hydrobromic acid, phosphoric acid and sulfuric acid, and, amongst organic acids, oxalic acid, maleic acid, fumaric acid, lactic acid, tartaric acid, malic acid, citric acid, salicylic acid, adipic acid and benzoic acid; other physiologically tolerated acids may be found in Fortschritte der Arzneimittelforschung, Vol. 10 (1966), 224–225, Birkhäuser Verlag, Basel and Stuttgart.

The addition salts with acids are as a rule obtained in a conventional manner, by mixing the free base, or a solution thereof, with the corresponding acid or a solution thereof in an organic solvent, for example a lower alcohol, eg. methanol, ethanol or propanol, or a lower ketone, eg. acetone, methyl ethyl ketone or methyl isobutyl ketone, or an ether, eg. diethyl ether, tetrahydrofuran and dioxane. Mixtures of the said solvents may also be used, to achieve better deposition of crystals. Furthermore, pharmaceutically acceptable aqueous solutions of addition salts of the phenylpiperazinyl derivatives of the general formula (I) with acids may be prepared by dissolving the free base of the general formula (I) in an aqueous hydrochloric acid solution.

The novel compounds, and their physiologically tolerated addition salts with acids, are useful as drugs, having a hypotensive action, for the treatment of hypertonia.

The hypotensive action was tested on rats, using, as the comparative compounds, the anti-hypertonic agent Urapidil (6-{3-[4-(2-methoxyphenyl)-piperazin-1-yl]-propylamino}-1,3-dimethyluracil).

Male Sprague-Dawley rats weighing 220–280 g were used, under urethane narcosis (1.78 g/kg, administered intraperitoneally) for the investigation. The blood pressure was measured directly in the carotid artery. The compound was administered intravenously into the jugular vein.

The dose (mg/kg) which caused a 20% reduction in blood pressure was determined as the ED 20%.

In addition to the hypotensive action, the acute toxicity (LD 50, mg/kg), for intraperitoneal administration, was determined for groups of 10 female NMRI mice, weighing 22–27 g.

The therapeutic range is the quotient of the LD 50 and the ED 20%.

The compounds according to the invention have a powerful hypotensive action. Table 1 shows that their activity is from 2.5 to 22.5 times as great as that of the comparative compound Urapidil. The therapeutic index is up to 13 times greater than that of Urapidil. Compared to the compounds of German Laid-Open Application DOS 2,811,638, the novel compounds are classifiable not as β-sympatholytic, but as selectively hypotensive or anti-hypertensive.

TABLE 1

| Compound of Example No. | Hypotensive action[1] | | Toxicity[3] LD 50 | Therapeutic index[4] |
|---|---|---|---|---|
| | ED 20% | R.A.[2] | | |
| 2 | 0.0221 | 8.55 | 56.2 | 2,540 |
| 7 | 0.0754 | 2.51 | 215 | 2,850 |
| 9 | 0.00840 | 22.50 | 215 | 25,600 |
| 10 | 0.0333 | 5.68 | 224 | 6,730 |
| 12 | 0.0195 | 9.69 | 162 | 8,300 |
| 16 | 0.0716 | 2.64 | 178 | 2,490 |
| Urapidil | 0.189 | 1.00 | 362 | 1,920 |

[1]Rat. Urethane narcosis. Intravenous administration.
[2]Relative activity. Urapidil = 1.00
[3]Mouse. Intraperitoneal administration
[4] $\frac{LD\ 50}{ED\ 20\%}$ Accordingly, the present invention also relates to therapeutic agents or formulations which in addition to conventional carriers and diluents contain a compound of the formula I, or a physiologically tolerated addition salt thereof with an acid, as the active compound, and to the use of the novel compounds in the treatment of hypertonia.

The novel compounds may be employed in the conventional solid or liquid pharmaceutical forms, such as tablets, capsules, powders, granules, dragees or solutions. These are prepared in a conventional manner, and to do so the active compounds can be mixed with the conventional pharmaceutical auxiliaries, such as talc, gum arabic, sucrose, lactose, cereal starch or corn starch, potato flour, magnesium stearate, alginates, gum tragacanth, carraghenates, polyvinyl alcohol, polyvinylpyrrolidone, aqueous or non-aqueous carriers, wetting agents, dispersants, emulsifiers and/or preservatives (cf. L. G. Goodman and A. Gilman, The Pharmacological Basis of Therapeutics). The formulations thus obtained normally contain from 0.001 to 99% by weight of the active compound.

The preferred formulations are those suitable for oral administration. Examples of these are tablets, film tablets, dragees, capsules, pills, powders, solutions, suspensions and depot forms. Parenteral formulations, such as injection solutions, may also be used. Suppositories are a further example of suitable formulations.

Appropriate tablets may be obtained, for example, by mixing the active compounds with conventional auxiliaries, for example inert diluents, such as dextrose, sugar, sorbitol, mannitol, polyvinylpyrrolidone, calcium carbonate, calcium phosphate or lactose, disintegrating agents, such as corn starch or alginic acid, binders, such as starch or gelatin, lubricants, such as magnesium stearate or talc, and/or agents for achieving a depot effect, such as carboxypolymethylene, carboxymethylcellulose, cellulose acetate phthalate or polyvinyl acetate. The tablets can also consist of a plurality of layers.

Similarly, dragees can be prepared by coating cores, prepared similarly to the tablets, with agents conventionally used in dragee coatings, for example collidone or shellac, gum arabic, talc, titanium dioxide or sugar. The dragee coating can also consist of a plurality of layers, and the auxiliaries mentioned above in connection with tablets may be used therein.

Solutions or suspensions containing the novel active compounds may additionally contain flavor improvers, such as vanillin or orange extract. They may also contain suspending agents, such as sodium carboxymethylcellulose, or preservatives, such as p-hydroxybenzoates. Capsules containing the active compounds may be prepared, for example, by mixing the active compound with an inert carrier, such as lactose or sorbitol, and encapsulating the mixture in gelatin capsules. Suitable suppositories can be prepared, for example, by mixing the active compounds with appropriate carriers, such as neutral fats or polyethylene glycol or their derivatives.

The dosage of the compounds according to the invention depends on the age, condition and weight of the patient and on the route of administration. As a rule, the daily dose of active compound is from 5 to 100, preferably from 10 to 80, mg.

The Examples which follow illustrate the present invention.

I. Preparation of starting compounds

I. ortho-1,3,4-Oxadiazol-2-yl-phenol 90 g (0.6 mole) of salicylic acid hydrazide and 355.2 g (2.4 moles) of orthoformic acid ethyl ester are refluxed for 22 hours. Excess of the ester is distilled off and the solid residue is recrystallized from ethanol. 62.9 g of colorless crystals (64.7% of theory) are obtained; melting point 112°–113° C.

II. ortho-(5-Methyl-1,3,4-oxadiazol-2-yl)-phenol 90 g (0.6 mole) of salicylic acid hydrazide and 388.8 g (2.4 moles) of triethyl orthoacetate in 500 ml of n-propanol are refluxed for 84 hours. When the mixture has cooled, the precipitate is filtered off and recrystallized from a mixture of toluene and petroleum ether. 47 g of colorless crystals (26.7% of theory) are obtained; melting point 74°–76° C.

III. meta-1,3,4-Oxadiazol-2-yl-phenol

This compound is prepared similarly to Example I. 83 g of colorless crystals (86% of theory) are obtained; melting point 215°–216° C.

IV. meta-(5-Methyl-1,3,4-oxadiazol-2-yl)-phenol

This compound is prepared similarly to Example II. 94 g of colorless crystals (89% of theory) are obtained; melting point 174°–175° C.

V. para-1,3,4-Oxadiazol-2-yl-phenol

This compound is prepared similarly to Example I. 87 g of colorless crystals (89.5% of theory) are obtained; melting point 215° C.

VI. para-(5-Methyl-1,3,4-oxadiazol-2-yl)-phenol

This compound is prepared similarly to Example II. 101 g of colorless crystals (96% of theory); melting point 232° C.

VII. 2,3-Epoxypropoxy-2-(1,3,4-oxadiazol-2-yl)-benzene

Following a method similar to Example VIII, 4.3 g (55% of theory) of a pale yellow oil are obtained. This compound has an NMR spectrum in accordance with expectations, namely: $^1$H-NMR (CDCl$_3$): $\delta = 8.5$ (1H, s, oxadiazole proton), $\delta = 7.0$–8.0 (4H, m, aromatic protons), $\delta = 4.2$ (2H, m), $\delta = 3.4$ (1H, m) and $\delta = 2.85$ (2H, d) for the epoxypropyl protons.

VIII. 2,3-Epoxypropoxy-2-(5-methyl-1,3,4-oxadiazol-2-yl)-benzene 1.6 g of sodium hydride, in the form of a 55% strength suspension in paraffin oil (0.036 mole) are introduced into 70 ml of anhydrous tetrahydrofuran and 6.3 g (0.036 mole) of ortho-(5-methyl-1,3,4-oxadiazol-2-yl)-phenol, dissolved in 50 ml of tetrahydrofuran, are added dropwise. 5 g (0.036 mole) of epibromohydrin are then introduced dropwise, 10 ml of hexamethylphosphorotriamide are added to the reaction mixture, and the whole is stirred for 32 hours at room temperature. Thereafter, the reaction mixture is poured into 500 ml of aqueous sodium chloride solution and repeatedly extracted by shaking with diethyl ether. The combined ether extracts are dried over anhydrous sodium sulfate and concentrated on a rotary evaporator to give a yellow oil. This crystallizes on triturating with a toluene/hexane mixture. 5.5 g (66% of theory) of colorless crystals are obtained; melting point 38°–40° C.

$C_{12}H_{12}N_2O_3$ (232); calculated C: 62.1, H: 5.2, N: 12.1; found C: 61.6, H: 5.3, N: 12.1.

IX. 2,3-Epoxypropoxy-3-(1,3,4-oxadiazol-2-yl)-benzene

Using a method similar to Example VIII, 4.2 g (53% of theory) of colorless crystals are obtained; melting point 80°–82° C.

X. 2,3-Epoxypropoxy-3-(5-methyl-1,3,4-oxadiazol-2-yl)-benzene

Using a method similar to Example VIII, 5.7 g (68% of theory) of colorless crystals are obtained; melting point 56° C.

XI. 2,3-Epoxypropoxy-4-(1,3,4-oxadiazol-2-yl)-benzene

Using a method similar to Example VIII, 5.4 g (69% of theory) of colorless crystals are obtained; melting point 81°–82° C.

$C_{11}H_{10}O_3N_2$ (218); calculated C: 60.6, H: 4.6, N: 12.8; found C: 61.2, H: 5.2, N: 12.4.

XII. 2,3-Epoxypropoxy-4-(5-methyl-1,3,4-oxadiazol-2-yl)-benzene

Using a method similar to Example VIII, 5.9 g (71% of theory) of colorless crystals are obtained; melting point 65°–67° C.

II. Preparation of the compounds according to the invention

EXAMPLE 1

1-[2-(1,3,4-Oxadiazol-2-yl)-phenoxy]-3-[4-(2-methoxyphenyl)-piperazin-1-yl]-propan-2-ol 7.3 g (0.033 mole) of 2,3-epoxypropoxy-2-(1,3,4-oxadiazol-2-yl)-benzene from Example VII and 6.4 g (0.033 mole) of 2-methoxy-phenylpiperazine in 50 ml of ethanol are refluxed for 17 hours. The solvent is stripped off on a rotary evaporator and the oily residue is taken up in methylene chloride. The solution is washed with 3×50 ml of water, dried over anhydrous sodium sulfate, filtered and concentrated. 12.6 g (93% of theory) of a pale yellow oil are obtained.

The hydrochloride (a hygroscopic product) is precipitated from a solution of the oil in an ethanol/diethyl ether mixture by adding a solution of hydrogen chloride in ether; it is filtered off, washed with isopropanol and dried at 80° C. under reduced pressure.

4.9 g (29% of theory) of colorless crystals are obtained; melting point 129°–130° C.

$C_{22}H_{26}N_4O_4 \cdot 1.5$ HCl·H$_2$O (482); calculated C 54.7, H 6.1, Cl 10.9, N 11.6, O 16.6; found C 54.8, H 6.7, Cl 10.0, N 11.8, O 16.5.

EXAMPLE 2

1-[2-(5-Methyl-1,3,4-oxadiazol-2-yl)-phenoxy]-3-[2-methoxyphenyl)-piperazin-1-yl]-propan-2-ol This compound is prepared by a method similar to Example 1. 3.1 g (20% of theory) of colorless crystals are obtained; melting point 248°–249° C.

$C_{23}H_{28}N_4O_4 \cdot$HCl (461); calculated C 59.9, H 6.3, Cl 7.6, N 12.2, O 13.9; found C 59.0, H 6.2, Cl 7.7, N 12.1, O 14.7.

EXAMPLE 3

1-[2-(1,3,4-Oxadiazol-2-yl)-phenoxy]-3-[4-methoxyphenyl)-piperazin-1-yl]-propan-2-ol 8.1 g (0.037 mole) of 2,3-epoxypropoxy-2-(1,3,4-oxadiazol-2-yl)-benzene from Example VII and 7.1 g (0.037 mole) of 3-methoxyphenylpiperazine in 100 ml of isobutanol are refluxed for 18 hours. The mixture is worked up similarly to Example 1. 11.1 g (62% of theory) of colorless crystals are obtained; melting point 126°–128° C.

$C_{22}H_{26}O_4N_4.2$ HCl (438); calculated C 54.7, H 5.8, Cl 14.7, N 11.6; found C 54.4, H 6.2, Cl 12.2, N 11.9.

EXAMPLE 4

1-[2-(5-Methyl-1,3,4-oxadiazol-2-yl)-phenoxy]-3-[4-(3-methoxyphenyl)-piperazin-1-yl]-propan-2-ol This compound is prepared by a method similar to Example 1. 11.6 g (66% of theory) of colorless crystals are obtained; melting point 201°–202° C.

$C_{23}H_{28}N_4O_4.2$ HCl.2 $H_2O$ (533); calculated C 51.8, H 6.4, N 10.5; found C 52.6, H 6.4, N 10.6.

EXAMPLE 5

1-[2-(5-Methyl-1,3,4-oxadiazol-2-yl)-phenoxy]-3-[4-(3-chlorophenyl)-piperazin-1-yl]-propan-2-ol This compound is prepared by a method similar to Example 3. 6.6 g (40% of theory) of colorless crystals are obtained; melting point 115°–117° C.

$C_{22}H_{25}ClN_4O_3.2$ HCl (501); calculated C 52.7, H 5.4, N 11.2; found C 52.4, H 5.5, N 11.1.

EXAMPLE 6

1-[2-(5-Methyl-1,3,4-oxadiazol-2-yl)-phenoxy]-3-[4-(4-fluorophenyl)-piperazin-1-yl]-propan-2-ol This compound is prepared by a method similar to Example 1, in isopropanol as the solvent. 6.6 g (41% of theory) of colorless crystals are obtained; melting point 212°–213° C.

$C_{22}H_{25}FN_4O_3.2$ HCl (485); calculated C 54.4, H 5.4, N 11.5, Cl 14.6; found C 54.1, H 5.8, N 11.4, Cl 14.3.

EXAMPLE 7

1-[3-(1,3,4-Oxadiazol-2-yl)-phenoxy]-3-[4-(2-methoxyphenyl)piperazin-1-yl]-propan-2-ol This compound is prepared by a method similar to Example 1, in ethanol as the solvent. 3.6 g (22% of theory) of colorless crystals are obtained; melting point 208°–210° C.

$C_{22}H_{26}N_4O_4.1.5$ HCl.1.5 $H_2O$ (492); calculated C 53.7, H 6.2, N 11.4; found C 53.2, H 6.5, N 11.0.

EXAMPLE 8

1-[3-(1,3,4-Oxadiazol-2-yl)-phenoxy]-3-[4-(3-methoxyphenyl)-piperazin-1-yl]-propan-2-ol This compound is prepared by a method similar to Example 1, in isopropanol as the solvent. 6.6 g (40% of theory) of colorless crystals are obtained; melting point 208°–209° C.

$C_{22}H_{26}N_4O_4.1.5$ HCl.1.5 $H_2O$ (492); calculated C 53.7, H 6.2, N 11.4; found C 53.4, H 6.4, N 11.3.

EXAMPLE 9

1-[3-(1,3,4-Oxadiazol-2-yl)-phenoxy]-3-[4-(2-ethoxyphenyl)-piperazin-1-yl]-propan-2-ol This compound is prepared by a method similar to Example 1, in isopropanol as the solvent. 13.4 g (79% of theory) of colorless crystals are obtained; melting point 211°–212° C.

$C_{23}H_{28}N_4O_4.2$ HCl (497); calculated C 55.4, H 6.0, N 11.3; found C 54.7, H 6.3, N 11.0.

EXAMPLE 10

1-[3-(5-Methyl-1,3,4-oxadiazol-2-yl)-phenoxy]-3-[4-(2-methoxyphenyl)-piperazin-1-yl]-propan-2-ol This compound is prepared by a method similar to Example 1, in isopropanol as the solvent. 11.2 g (68.6% of theory) of colorless crystals are obtained; melting point 205°–206° C.

$C_{23}H_{28}N_4O_4.2$ HCl (497); calculated C 55.5, H 6.1, N 11.3, Cl 14.3; found C 55.4, H 6.2, N 11.4, Cl 14.0.

EXAMPLE 11

1-[3-(5-Methyl-1,3,4-oxadiazol-2-yl)-phenoxy]-3-[4-(3-methoxyphenyl)-piperazin-1-yl]-propan-2-ol This compound is prepared by a method similar to Example 1, in ethanol; the free piperazine derivative crystallizes out from the reaction solution and is filtered off. 10.1 g (72% of theory) of colorless crystals are obtained; melting point 125°–127° C.

$C_{23}H_{28}N_4O_4$ (424); calculated C 65.1, H 6.6, N 13.2; found C 64.9, H 6.6, N 13.3.

EXAMPLE 12

1-[3-(5-Methyl-1,3,4-oxadiazol-2-yl)-phenoxy]-3-[4-(2-ethoxyphenyl)-piperazin-1-yl]-propan-2-ol This compound is prepared by a method similar to Example 1, in isopropanol as the solvent. 14.6 g (87% of theory) of colorless crystals are obtained; melting point 200°–202° C.

$C_{24}H_{30}N_4O_4.2$ HCl (511); calculated C 56.4, H 6.3, N 11.0, Cl 13.9; found C 56.3, H 6.3, N 11.1, Cl 13.8.

EXAMPLE 13

1-[4-(1,3,4-Oxadiazol-2-yl)-phenoxy]-3-[4-(3-methoxyphenyl)-piperazin-1-yl]-propan-2-ol This compound is prepared by a method similar to Example 1, in isopropanol as the solvent; the free piperazine derivative crystallizes out direct from the reaction solution, and is filtered off. 12 g (98% of theory) of colorless crystals are obtained; melting point 149°–150° C.

$C_{22}H_{26}N_4O_4$ (410); calculated C 64.4, H 6.4, N 13.6; found C 64.1, H 6.5, N 13.4.

EXAMPLE 14

1-[4-(1,3,4-Oxadiazol-2-yl)-phenoxy]-3-[4-(4-fluorophenyl)-piperazin-1-yl]-propan-2-ol This compound is prepared by a method similar to Example 1, in isopropanol as the solvent; the free piperazine derivative crystallizes out direct from the reaction solution, and is filtered off. 11.1 g (81% of theory) of colorless crystals are obtained; melting point 226°–228° C.

$C_{21}H_{23}FN_4O_3.H_2O$ (416); calculated C 60.6, H 6.1, N 13.4; found C 60.8, H 6.4, N 12.4.

The following are further compounds according to the invention which we have prepared:

EXAMPLE 15

1-[3-(5-Methyl-1,3,4-oxadiazol-2-yl)-phenoxy]-3-[4-(3-chlorophenyl)-piperazin-1-yl]-propan-2-ol (.2 HCl), melting point 172°–173° C.

EXAMPLE 16

1-[3-(5-Methyl-1,3,4-oxadiazol-2-yl)-phenoxy]-3-[4-(2-chlorophenyl)-piperazin-1-yl]-propan-2-ol (.2 HCl.H$_2$O), melting point 216°–218° C.

EXAMPLE 17

1-[3-(1,3,4-Oxadiazol-2-yl)-phenoxy]-3-[4-(2-chlorophenyl)-piperazin-1-yl]-propan-2-ol, melting point 130°–132° C.

EXAMPLE 18

1-[3-(1,3,4-Oxadiazol-2-yl)-phenoxy]-3-[4-(2,6-dimethylphenyl)-piperazin-1-yl]-propan-2-ol (.HCl), melting point 222°–223° C.

EXAMPLE 19

1-[3-(5-Methyl-1,3,4-oxadiazol-2-yl)-phenoxy]-3-[4-(2,6-dimethylphenyl)-piperazin-1-yl]-propan-2-ol (.HCl), melting point 187°–188° C.

EXAMPLE 20

1-[3-(5-Methyl-1,3,4-oxadiazol-2-yl)-phenoxy]-3-[4-(2,4-dimethoxyphenyl)-piperazin-1-yl]-propan-2-ol (.2.5 HCl.0.5 H$_2$O), melting point 195°–198° C.

EXAMPLE 21

1-[3-(1,3,4-Oxadiazol-2-yl)-phenoxy]-3-[4-(2,4-dimethoxyphenyl)-piperazin-1-yl]-propan-2-ol, melting point 144°–147° C.

EXAMPLE 22

1-[3-(1,3,4-Oxadiazol-2-yl)-phenoxy]-3-(4-phenyl-piperazin-1-yl)-propan-2-ol, melting point 136°–138° C.

EXAMPLE 23

1-[3-(5-Methyl-1,3,4-oxadiazol-2-yl)-phenoxy]-3-[4-phenyl-piperazin-1-yl]-propan-2-ol.

EXAMPLE 24

1-[3-(5-Methyl-1,3,4-oxadiazol-2-yl)-phenoxy]-3-[4-(4-methoxyphenyl)-piperazin-1-yl]-propan-2-ol, melting point 166°–168° C.

EXAMPLE 25

1-[4-(1,3,4-Oxadiazol-2-yl)-phenoxy]-3-[4-(2-methoxyphenyl)-piperazin-1-yl]-propan-2-ol (.2 HCl.H$_2$O), melting point 225° C.

EXAMPLE 26

1-[4-(1,3,4-Oxadiazol-2-yl)-phenoxy]-3-[4-(2-chlorophenyl)-piperazin-1-yl]-propan-2-ol (.2 HCl), melting point 249°–251° C.

EXAMPLE 27

1-[4-(5-Methyl-1,3,4-oxadiazol-2-yl)-phenoxy]-3-[4-(2-methoxyphenyl)-piperazin-1-yl]-propan-2-ol (.oxalate.H$_2$O), melting point 162°–163° C.

EXAMPLE 28

1-[4-(5-Methyl-1,3,4-oxadiazol-2-yl)-phenoxy]-3-[4-(3-methoxyphenyl)-piperazin-1-yl]-propan-2-ol (.2.5 HCl.H$_2$O), melting point 230°–233° C.

EXAMPLE 29

1-[4-(1,3,4-Oxadiazol-2-yl)-phenoxy]-3-[4-(2,4-dimethoxyphenyl)-piperazin-1-yl]-propan-2-ol, melting point 161° C.

III. Examples of formulations prepared in a conventional manner

1. Tablets:

| | |
|---|---|
| (a) An active compound of the formula I | 5 mg |
| Lactose | 200 mg |
| Methylcellulose | 15 mg |
| Corn starch | 50 mg |
| Talc | 11 mg |
| Magnesium stearate | 4 mg |
| (b) An active compound of the formula I | 20 mg |
| Lactose | 178 mg |
| Avicel | 80 mg |
| Polywachs 6000 | 20 mg |
| Magnesium stearate | 2 mg |
| (c) An active compound of the formula I | 50 mg |
| Polyvinylpyrrolidone (mean molecular weight 25,000) | 170 mg |
| Polyethylene glycol (mean molecular weight 4,000) | 14 mg |
| Hydroxypropylmethylcellulose | 40 mg |
| Talc | 4 mg |
| Magnesium stearate | 2 mg |

(c) The active compound is moistened with a 10% strength aqueous solution of the polyvinylpyrrolidone, forced through a sieve of 1.0 mm mesh size, and dried at 50° C. The granules obtained are mixed with polyethylene glycol (mean molecular weight 4,000), hydroxypropylmethylcellulose, talc and magnesium stearate and the mixture is pressed to form tablets each weighing 280 mg.

2. Example of dragees

| | |
|---|---|
| An active compound of the formula I | 60 mg |
| Lactose | 90 mg |
| Corn starch | 60 mg |
| Polyvinylpyrrolidone | 6 mg |
| Magnesium stearate | 1 mg |

The active compound, lactose and corn starch are mixed, moistened with an 8% strength aqueous solution of the polyvinylpyrrolidone and forced through a 1.5 mm sieve; the granules obtained are dried at 50° C. and then forced through a 1.0 mm sieve. The granules thus obtained are mixed with magnesium stearate and the mixture is molded to form dragee cores. These are coated in a conventional manner with a coating essentially consisting of sugar and talc.

3. Capsule formation

| | |
|---|---|
| An active compound of the formula I | 5 mg |
| Magnesium stearate | 2.0 mg |
| Lactose | 19.3 mg |

4. Injection solution

| | |
|---|---|
| An active compound of the formula I | 10 mg |
| Sodium chloride | 9 mg |
| Distilled water, q.s. | |

-continued

| to make 1.0 ml |
| --- |

We claim:
1. A compound of the formula I

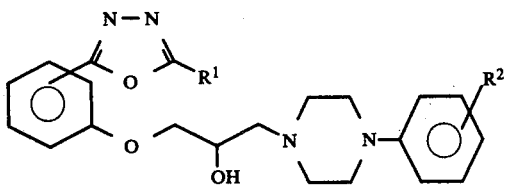

where $R^1$ is hydrogen or lower alkyl of 1 to 4 carbon atoms and $R^2$ is hydrogen, halogen, lower alkyl of 1 to 4 carbon atoms or lower alkoxy of 1 to 3 carbon atoms, and where the phenyl ring may contain one or two substituents $R^2$, and its physiologically tolerated addition salts with acids, the 1,3,4-oxadiazol-2-yl radical being in the o- or m- position to the ether group.

2. A compound of the formula I as set forth in claim 1, wherein $R^1$ is hydrogen or methyl and $R^2$ is fluorine, chlorine, methoxy or ethoxy, and the 1,3,4-oxadiazol-2-yl radical is in the m-position to the ether group, and its physiologically tolerated addition salts with acids.

3. 1-[3-(5-Methyl-1,3,4-oxadiazol-2-yl-phenoxy]-3-[4-(2-methoxyphenyl)-piperazin-1-yl]-propan-2-ol and its physiologically tolerated addition salts with acids.

4. A therapeutic agent, for the treatment of hypertonia, which contains a compound of the formula I, or a physiologically tolerated addition salt thereof with an acid, as the active compound, together with conventional carriers and diluents.

5. A therapeutic agent as set forth in claim 4, which contains 1-[3-(5-methyl-1,3,4-oxadiazol-2-yl-phenoxy]-3-[4-(2-methoxyphenyl)-piperazin-1-yl]-propan-2-ol or a physiologically tolerated addition salt thereof with an acid.

6. A compound as set forth in claim 1, wherein $R^2$ is in the o- position.

* * * * *